United States Patent [19]

Pearson

[11] Patent Number: 4,901,563
[45] Date of Patent: Feb. 20, 1990

[54] SYSTEM FOR MONITORING FLUIDS DURING WELL STIMULATION PROCESSES

[75] Inventor: C. Mark Pearson, Plano, Tex.

[73] Assignee: Atlantic Richfield Company, Los Angeles, Calif.

[21] Appl. No.: 350,985

[22] Filed: May 11, 1989

Related U.S. Application Data

[62] Division of Ser. No. 243,546, Sep. 13, 1988, Pat. No. 4,845,981.

[51] Int. Cl.⁴ .............................................. E21B 43/26
[52] U.S. Cl. ....................................... 73/151; 166/308
[58] Field of Search ........................... 73/53, 151, 155; 166/250, 305.1, 308

[56] References Cited

U.S. PATENT DOCUMENTS 4,541,935  9/1985  Constien et al. ..................... 166/308
4,700,567  10/1987  Frey et al. .............................. 73/151

Primary Examiner—John Chapman
Assistant Examiner—Kevin D. O'Shea
Attorney, Agent, or Firm—Michael E. Martin

[57] ABSTRACT

Certain wellbore fluid stimulation treatments may be monitored by a system including instrumented manifolds which may be connected between a base fluid source and a blending unit and between the blending unit and fluid injection pumps, respectively for measuring flow rates of the base fluid, the fluid additives and the fluid composition formed by the base fluid and the fluid additives. Instruments are also provided for measuring fluid temperature, pH, viscosity and flow behavior indexes (n', K') and fluid density. Quality control and determination of pressure losses in the wellbore together with modeling of stimulation treatments may be carried out by the continuous monitoring of parameters with the base fluid manifold and the mixed composition manifold.

7 Claims, 4 Drawing Sheets

SYSTEM FOR MONITORING FLUIDS DURING WELL STIMULATION PROCESSES

This is a division of application Ser. No. 243,546, filed Sept. 13, 1988, now U.S. Pat. No. 4,845,981.

BACKGROUND OF THE INVENTION

1. Field of the Invention

The present invention pertains to a system for measuring certain properties of fluids, such as pressures, flow rates, temperature, viscosity and density for fluids used in certain well stimulation processes including hydraulic fracturing.

2. Background

In certain well stimulation processes, such as hydraulic fracturing, the properties of the fluid being injected into a formation and the fluid flow conditions are critical to the success of the stimulation process. Typically, a so-called oil field service company performs the stimulation treatment by supplying mixing and pumping equipment and fluids for injection into the well under a specification supplied by the owner of the formation or reservoir into which the fluid is being injected. The cost associated with certain stimulation treatments and the criticality of the treatment as regards preventing damage to the formation make it highly desirable to provide continuous onsite monitoring of the fluid properties during the stimulation process.

If the treatment process is unsuccessful there is often insufficient information to evaluate the cause of the failure of the process. In this regard it has been recognized that it is important to be able to accurately and continuously measure and record certain fluid parameters during processes such as hydraulic fracturing so that real time analysis of the data collected can improve operational understanding and possibly apply new technology to stimulation processes. The lack of concern for this type of data collection in the past has failed to bring any attention to the need for specialized equipment which is desirable to handle the high volume flow rates of specialized fluids. However, the development of relatively small, portable computers adapted for handling complex data streams has also provided the possibility of an onsite fluid data acquisition and computation system which enables the engineer to continuously monitor the properties of the fluid during the performance of the fluid injection process. It is to this end that the present invention has been directed with a view to providing a system for measuring certain fluid properties and parameters during certain well processes such as hydraulic fracturing and other enhanced oil recovery techniques.

SUMMARY OF THE INVENTION

The present invention provides an improved system for monitoring certain properties and parameters of fluids during processes which involve injection of fluids into a subterranean formation such as in hydraulic fracturing and flooding processes.

In accordance with one aspect of the present invention, there has been developed an improved system for continuously measuring and recording certain fluid parameters during a stimulation process, such as hydraulic fracturing, wherein wellhead as well as bottom-hole pressures are measured and calculated, respectively, and flow rates of fluid components and the fluid mixture being injected are monitored. Certain properties of the major component of the fluid being injected as well as the fluid composition or mixture being injected itself are measured and recorded including temperature, pH, viscosity, the Power Law coefficients such as the consistency index (K') and the Power Law or flow behavior index (n') and the fluid density and these properties are utilized in calculating certain other flow conditions which are desired to be known.

In accordance with another aspect of the present invention, there is provided a system for measuring fluid properties of a major component of a stimulation fluid mixture or composition as well as the same or similar properties of the fluid composition with certain additives incorporated therein, such as gellable fracturing fluids which include proppant materials and additives such as leak-off control agents and the like.

The system of the present invention is advantageously constructed to provide for two instrumented manifold assemblies which each include an arrangement of instruments for determining fluid pressures, temperatures, viscosities and densities whereby the monitoring of these properties provides improved control over stimulation processes and process analysis. One of the manifolds is utilized in determining the fluid properties of the base fluid while the other manifold determines the properties of the fluid just prior to injection into the wellbore and after the addition of certain additives including proppants. The determination of the flow behavior indexes of the base fluid provides for calculation of the behavior of the fluid during a fracture process so that more accurate control over the process may be obtained.

The manifolds are uniquely constructed to minimize fluid pressure losses, settling out of entrained solids in the fluid stream and minimal wear and servicing of the instrument assemblies of the systems. The respective manifolds are advantageously provided as two separate skid mounted assemblies for use on or about a wellsite.

The above-described aspects of the present invention together with other advantages and superior features will be further appreciated by those skilled in the art upon reading the detailed description which follows in conjunction with the drawing.

DESCRIPTION OF A PREFERRED EMBODIMENT

Figure 1:
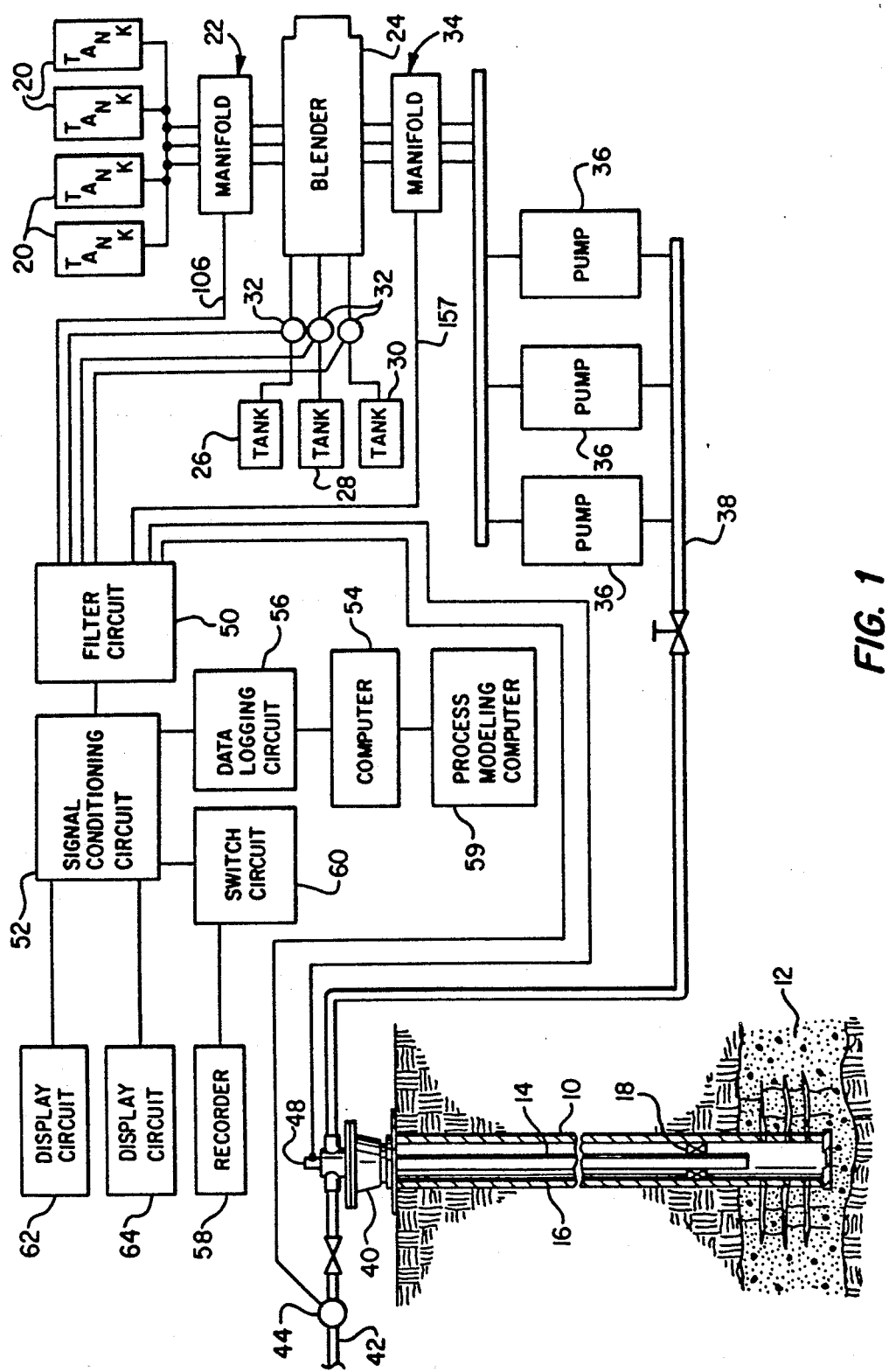
FIG. 1 is a general schematic diagram of the system of the present invention for use in a hydraulic fracturing process of an earth formation through an injection well.

In the description which follows, like parts are marked throughout the specification and drawing with the same reference numerals, respectively. The drawing figures are not necessarily to scale and certain features and components may be shown in schematic form and described generally with reference to commercial sources in the interest of clarity and conciseness.

Referring to FIG. 1, there is illustrated a schematic block diagram indicating major components of the system of the present invention. In particular, the system illustrated in FIG. 1 has been adapted for monitoring and analyzing certain properties of a fluid composition for injection into a wellbore 10 to hydraulically fracture a zone of interest in an earth formation 12. Pressure fluid may be injected into the formation 12 through a tubing string 14 and suitable perforations in a casing 16 in an isolated area below a packer or the like 18. In many hydraulic fracturing processes a gel-like fluid is prepared which is then mixed with gelling accelerators, retarders, leak-off control agents, and a proppant for injection into the formation to fracture the formation and prop open the resultant cracks or fractures. In order to minimize pumping requirements, the fluid is composed in such a way that gellation occurs at wellbore temperatures in the region of interest to be fractured. The injected fluid or slurry is, in many instances, ninety percent (90%) to ninety-five percent (95%) composed of a base fluid or gel which is typically stored in one or more storage tanks 20 brought on site for the fracturing process. The flow rates encountered in hydraulic fracturing may, in many instances, exceed 50 to 100 barrels per minute (2100 to 4200 gallons per minute). In order to monitor the quality of the base gel in the tanks 20 an instrument manifold, generally designated by the numeral 22 and to be described in further detail herein, is connected to the tanks 20 for measuring the properties of the base gel fluid before this fluid is injected or conducted to a blender apparatus generally designated by the numeral 24. In the blender apparatus 24 certain components are mixed with the base gel fluid such as a proppant stored in a storage tank or the like 26. Other fluids such as gel cross linking additives are added in the blender from a source 28 and a leak-off or fluid loss additive is added to the base gel in the blender from a source 30. Each of the sources 26, 28 and 30 preferably is in communication with the blender through respective flow meters 32 for monitoring the flow rate of these additives as they are added and mixed with the base gel fluid.

The fluid composition developed in the blender 24 is conducted to a second instrument manifold 34 wherein essentially the fluid properties measured in the instrument manifold 22 are measured again and these measurements are used to calculate expected bottom hole pressures in the wellbore in the vicinity of the formation 12. A sample of the fluid flowing through the instrument manifold 34 may also be subjected to bottom hole temperature conditions to measure the change in viscosity brought about by the expected temperature in the formation region of interest. The particular properties measured at the instrument manifolds 22 and 34 will be discussed in further detail hereinbelow together with discussion of the construction and features of these manifolds. The manifold 34 is typically connected to one or more high pressure pumps 36 which in turn may be connected to a pump discharge manifold 38 leading to wellhead 40 for conducting the fracturing fluid into the wellbore through the tubing 14. The wellhead 40 is also configured to include a flow back conduit 42 in which a flow meter 44 is interposed for measuring the flow rate of fluids coming out of the wellbore under certain test or operating conditions.

The various signal transmitting transducers or instruments associated with the manifolds 22 and 34 as well as signals from the flow meters 32 and 44 and a wellhead pressure transducer 48 are conducted to a suitable junction box and filtering circuit 50 and then to a signal conditioning circuit 52 whereby the signals from each of the instruments on the instrument manifolds 22 and 34 and the flow meters and pressure transducers illustrated specifically in FIG. 1 are conditioned for digital transmission to a computer 54. A data logging circuit 56 is interposed between the conditioning circuit 52 and the computer 54. A chart recorder 58 may also be arranged in circuit with the signal conditioning circuit 52, the computer 54 and the data logging circuit 56 by way of a selecting switch circuit 60 for chart recording of certain output signals from the instruments associated with the system. Certain totals of the measured parameters associated with the manifolds 22 and 34, for example, may be displayed through a circuit 62 and continuous visual display of the signals conditioned by the circuit 52 may be displayed through a circuit 64. A process modelling computer 59 is operably associated with the computer 54 for using data from the computer 54 to monitor the progress or changes in specifications of a stimulation process, for example.

Figure 2:
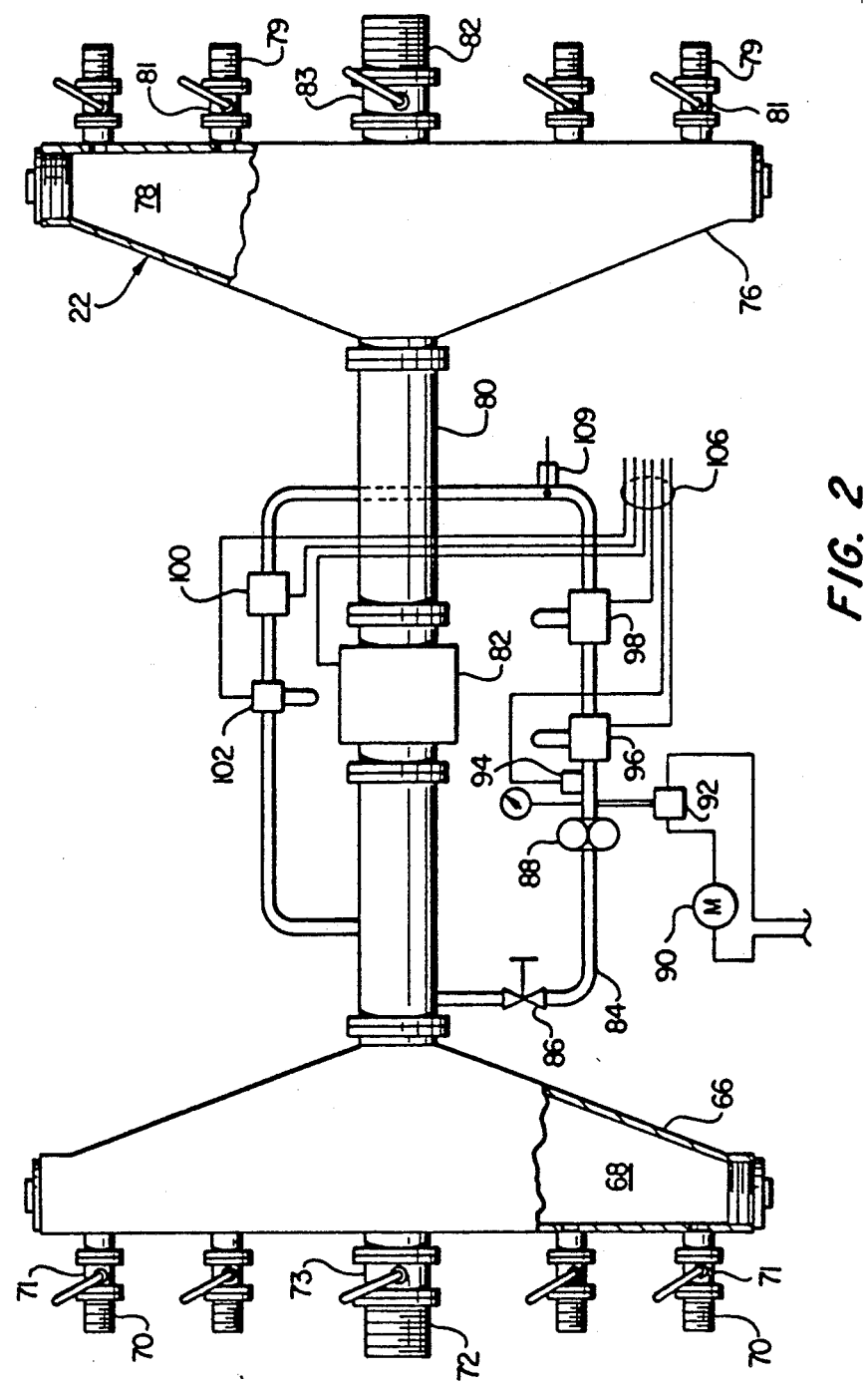
FIG. 2 is a plan view of an instrument manifold used for measuring the fluid properties of the major fluid component used in a hydraulic fracturing process.

Referring now to FIG. 2, the instrument manifold 22 includes a first manifold member 66 having an interior chamber 68 which is adapted to be in communication with a plurality of fluid inlet or outlet conduits 70 and 72 which are of selected pipe sizes to provide for connecting the manifold 22 to various sources of fluid. Each of the conduits 70 and 72 is preferably provided with a shutoff valve 71 or 73 interposed therein, respectively. The manifold member 66 is in communication with a second manifold member 76 having an interior chamber 78 by way of a conduit 80 having a flow meter 82 interposed therein. The manifold member 76 is also provided with plural conduits 79 and 82 each provided with a shutoff valve 81 and 83, respectively. Volumetric flow rate of fluid through the instrument manifold 22 is measured by the flow meter 82 which may be a turbine type manufactured by Halliburton Company, Dallas, Texas. Certain parameters of the fluid being pumped through the instrument manifold 22 are desired to be measured by a sampling conduit loop 84 in communication with the conduit 80 by way of a shutoff valve 86. A positive displacement rotary pump 88 is interposed in the conduit 84 and is motor driven by motor means 90 through a circuit which includes a pressure sensing shutoff switch 92. Fluid pressure in the conduit 84 is also sensed by a transducer 94.

The quality of the fluid being pumped through the instrument manifold 22 may be measured by two rotary viscometers 96 and 98 which are interposed in the conduit 84. The flow rate through the conduit 84 is also measured by a flow meter 100 and the pH of the fluid being conducted through the instrument manifold 22 is measured by a pH meter 102. Output signals indicating the parameters measured by each of the instruments 96, 98, 100 and 102 and sensors are conducted via a conductor bundle 106 to the signal conditioning circuit 50, FIG. 1.

It is, of course, assumed that the density of the fluid being pumped into the wellbore is known and, by operating the viscometers 96 and 98 at different shear rates, the apparent viscosity of the fluids measured at these rates may be used to determine the consistency index (K') and the Power Law or flow behavior index (n'). These indexes may be used to calculate the shear rate and the apparent viscosity of the fracture fluid in the fracture itself for purposes of controlling and evaluating the fracture process. The viscometers 96 and 98 may be of a type manufactured by Brookfield Engineering Laboratories of Stoughton, Mass. as their type TT1100. The flow meter 100 and the pH meter 102 may also be of types commercially available such as a magnetic type flow meter manufactured by Fischer and Porter Company and a pH meter manufactured by Foxboro Instruments, Inc. A temperature sensor 109 is interposed in the conduit 84 and is adapted to monitor the temperature of the fluid flowing through the instrument manifold 22.

The manifold 22 provides for monitoring the quality of the fluid which, in a hydraulic fracturing operation, makes up approximately 95% of the total fluid composition which is pumped into the wellbore. The addition of components such as proppants, gel setting agents and fluid loss control agents such as added by way of the flow meters 32 to the blender 24 make up the additional 5% of the total composition which is then monitored by the instrument manifold 34. The flow rates of the these additives are, of course, monitored and recorded by signals transmitted from the flow meters 32 to the computer 54 by way of the circuitry above-described.

Figure 3:
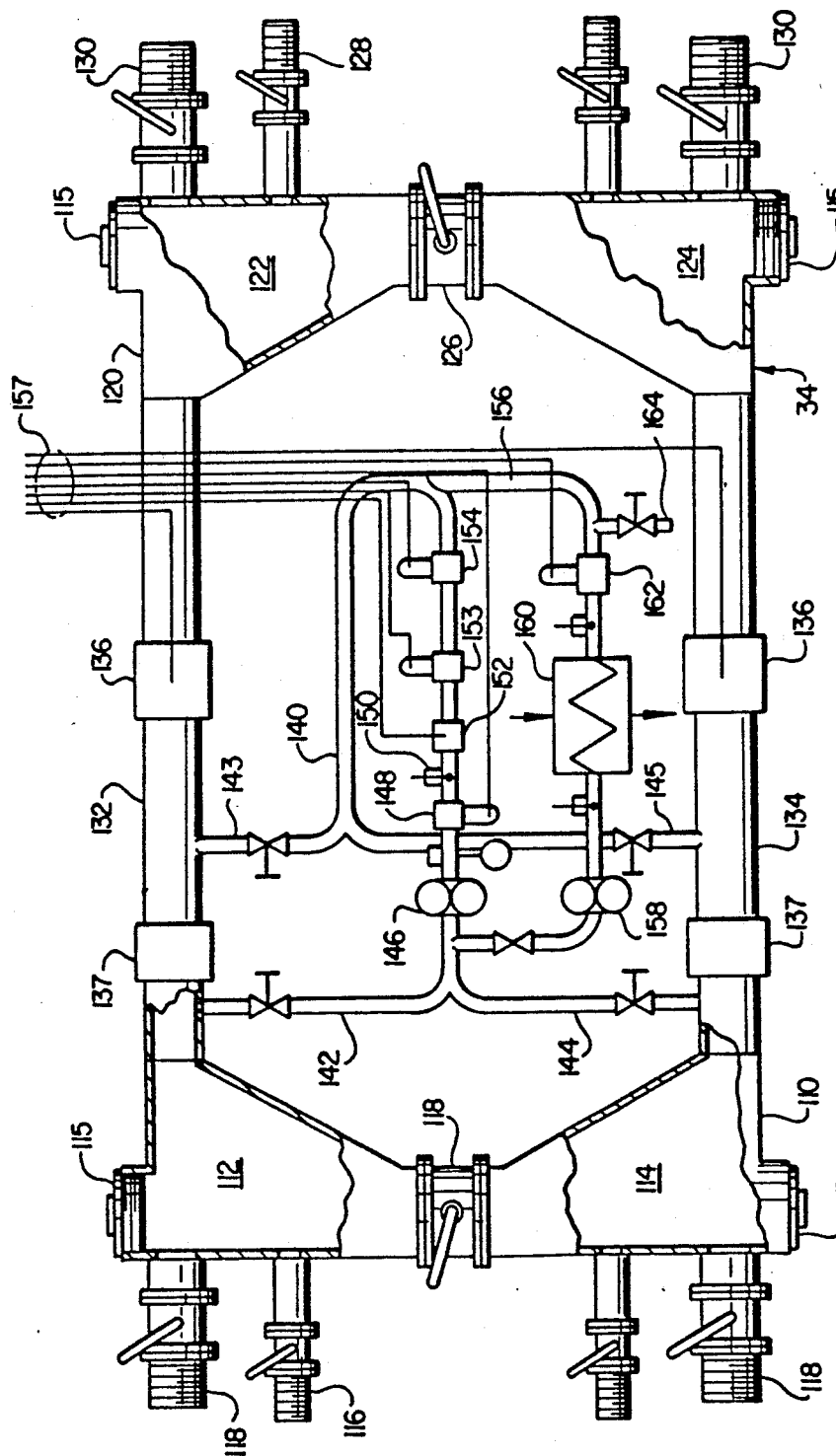
FIG. 3 is a plan view of an instrument manifold for conducting a slurry-like fluid composition used in hydraulic fracturing.

Referring now to FIG. 3, the instrument manifold 34 is characterized by a first manifold member 110 having respective manifold chambers 112 and 114 formed therein and, respectively, in communication with inlet conduits 116 and 118 of selected pipe sizes for accommodating the conduit connections available from the blender 24. The chambers 112 and 114 may be placed in communication with each other by way of a shutoff valve 118 or closed off from communication with each other by the valve. The manifold member 110 has been advantageously provided with removable cleanout plugs 115 in the event of accumulations of solids such as the proppants and leakoff control agents used in certain fracturing operations. The manifold 34 further includes a discharge manifold member 120 having respective manifold chambers 122 and 124 formed therein and operable to be placed in communication with each other or closed off from communication with each other by a valve 126. Selected sizes of discharge conduits 128 and 130 are in communication with the manifold member 120. The manifold member 120 is also advantageously provided with removable cleanout plugs 115.

The manifold members 110 and 120 are interconnected by parallel conduits 132 and 134, each of which is provided with a suitable volumetric flow meter 136 and a densimeter 137 interposed therein. If the flow rate of fluid required for a particular well stimulation or treatment process is sufficiently high to provide adequate flow velocities through the manifold members 110 and 120, the valves 118 and 126 are placed in their open positions so that the chambers 112 and 114 of the member 110 are in communication with each other and the chambers 122 and 124 of the manifold member 120 are in communication with each other. Total flow through the manifold 34 is measured by totalizing the flow rates measured by the respective flow meters 136. However, if the flow rate required for a particular well treatment process is reduced to a point wherein the additive solids in the fluid flowing through the manifold may tend to settle out, the valves 118 and 126 may be closed and only one of the conduits 132 or 134 is utilized to conduct flow through the manifold 34 so that flow velocities are maintained sufficiently high to prevent disentrainment of the solids.

Referring further to FIG. 3, the instrument manifold 34 includes a fluid sampling conduit loop 140 including branch conduits 142 and 144 for sampling the flow through the respective conduits 132 and 134. The conduit loop 140 includes return conduits 143 and 145 connected to the respective main flow conduits 132 and 134. The conduit loop 140 has interposed therein a rotary positive displacement pump 146, a pH meter 148, a temperature sensor 150, a densimeter 152 and viscometers 153 and 154. A secondary sample conduit loop 156 includes a pump 158 interposed therein, a heat exchanger 160 and a viscometer 162. A sampling port 164 is also provided for withdrawing a sample of the fluid flowing through the manifold 34. The fluid being conducted through the manifold 34 may be sampled to determine its various properties as measured by the pH meter 148, the densimeter 152 and the viscometers 153 and 154 by appropriate opening and closing of valves interposed in the conduit loop 140. For example, if flow is being conducted through both conduits 132 and 134 the sample conduit loop 140 receives flow from both branch conduits 142 and 144 and returns flow through the return conduits 143 and 145. Representative conductors are illustrated in FIG. 3 over which electrical signals from the instruments in the manifold 34, including the conduit loops 140 and 156, are transmitted by way of a conductor bundle 157 to the circuit 50.

The sample conduit loop 156 is adapted to determine the change in viscosity of the fluid as might be affected by a temperature increase or decrease sustained through the heat exchanger 160. Temperatures are, of course, measured at the inlet and outlet sides of the heat exchanger 160 to verify the conditions of the fluid before and after heating and before flowing through the viscometer 162. For example, if a fracturing fluid being monitored includes an additive which retards gellation until a certain temperature corresponding to the wellbore temperature is reached, the effectiveness of this additive may be sampled by conducting flow through the conduit loop 156 while measuring the change in viscosity sensed by the viscometer 162 as compared with the viscosity measured by the viscometers 153 and 154. The viscometers 153, 154 and 162 may also be of the type manufactured by Brookfield Engineering Laboratories as described hereinabove. The flowmeters 136 are of a type manufactured by Fischer and Porter Company of Warminster, Penna. and the densimeters 137 and 152 may be of a type manufactured by Texas Nuclear Company of Austin, Tex.

Figure 4:
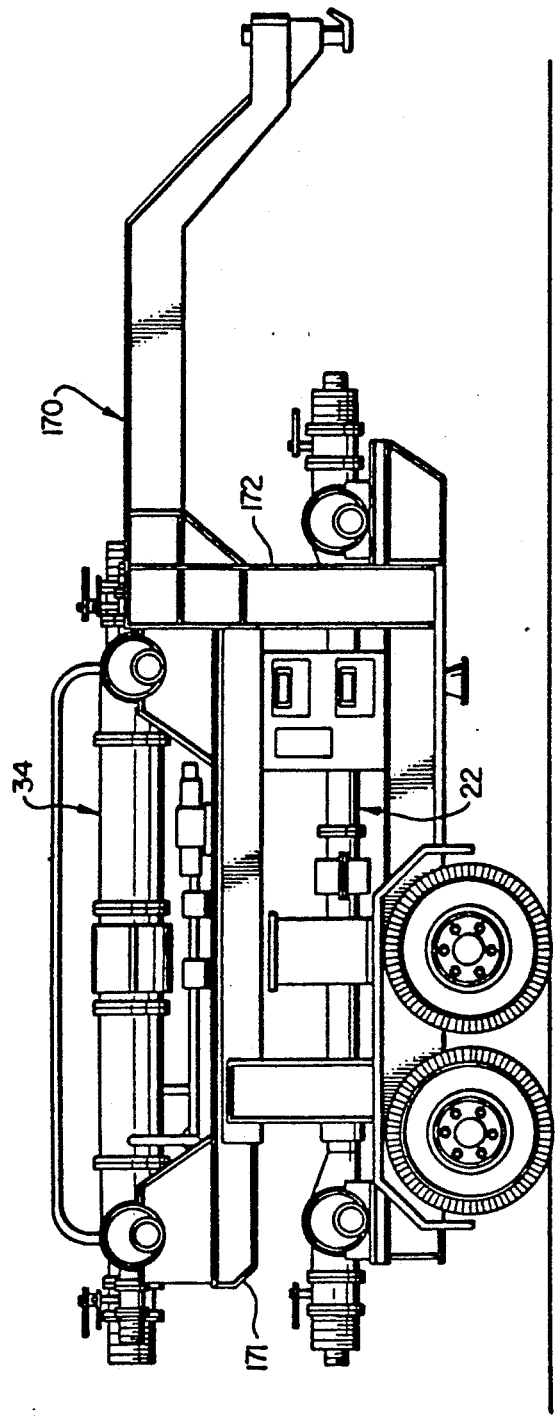
FIG. 4 is a side elevation of a transport vehicle having the manifolds of FIGS. 2 and 3, disposed thereon.

It is preferable that the system illustrated and described herein in FIGS. 1 through 3 be substantially portable for being transported from one well site to another. As illustrated in FIG. 4, there is provided a tandem axle, over-the-road, semitrailer, generally designated by the numeral 170 having a suitable frame 172 on which the manifolds 22 and 34 are mounted. The manifold 34 is preferably mounted on a conventional skid 171 and is easily removable by a crane or the like, not shown, for placement at a wellsite while the manifold 22 is supported by and secured to the trailer frame. The control and recording system characterized by the signal conversion circuit 52 and the computers 54 and 59 may be housed in a suitable enclosure, not shown, preferably vehicle mounted for transport also to and from a well site. Although the parameters measured by the instrument manifold 34 are duplicates in some respects of the parameters measured by the manifold 22, some variation in parameters is experienced due to the additives which are mixed with the base fluid in the blender 24. Moreover, particularly when pumping abrasive fracturing fluids, the instruments on the manifold 34 are subject to rapid wear and possible failure in the field, hence it is advantageous to provide an instrument manifold for measuring fluid properties which is disposed between the storage means for the relatively clean nonabrasive base fluid and the fluid after the addition of proppants and other additives.

The operation of the system described hereinabove is believed to be readily apparent to those skilled in the art. By providing the separate instrument manifolds for measuring the condition of the wellbore treatment fluid before the addition of any additives a quality check on this fluid is continuously available. The calculation of parameters such as the Power Law Indexes (K') and (n') provides a quality control check on the fluid, provides for calculation of friction pressure losses in the wellbore conduit so that bottomhole pressures may be more accurately monitored and provides input data for any process programs which may be used to model the progression of a fracturing process, for example. The system described herein may be modified to determine the expected pressure drop through the conduit 14, whose diameter and length are known, and using equations found in copending U.S. Patent Application S.N. 07/113,782 and U.S. Pat. No. 4,762,219, both to C. Mark Pearson et al. and assigned to the assignee of the present invention. The system described herein further provides a record or database of information including the parameters described above so that reference may be had to the conditions of the fluid being injected into the wellbore during the treatment process and comparisons of such parameters as average pressures, flow rates, total volumes and weights of material added to the fluid may be obtained and compared to the design parameters for the particular process. Although commercially available instruments are utilized in the system of the present invention, the viscometers may be modified in accordance with the type of viscometer described in U.S. Pat. No. 4,726,219 and publication no. SPE 16903, Society of Petroleum Engineers, entitled: "Development and Application of an Operator's Stimulation Monitoring System", by C. Mark Pearson. Conventional engineering materials may be used for the system including the instrument manifolds 22 and 34.

Although a preferred embodiment of the present invention has been described in detail herein, those skilled in the art will recognize that various substitutions and modifications may be made to the particular system described without departing from the scope and spirit of the invention as recited in the appended claims.

What is claimed is:

1. A method for monitoring the quality of a fluid composition for injection into a wellbore for performing a formation treatment process, said method comprising the steps of:

providing at least a first instrument manifold adapted to be interposed between a source of fluid and pump means for pumping said fluid to a wellbore, said first manifold including first and second manifold members interconnected by flow conduit means, said manifold members each including respective fluid inlet and outlet conduit connectors for connecting said first manifold to a source of fluid and to conduit means for conducting fluid from said first manifold, and a sample flow conduit connected to said first manifold for receiving a sample of fluid flow through said first manifold, said sample flow conduit including viscometer means interposed therein;

conducting liquid through said sample flow conduit at selected flow rates;

measuring at least the apparent viscosity of said fluid at respective selected shear rates of said fluid; and determining at least one of the consistency index (K') and the Power Law Index (n') of said fluid prior to injection of said fluid into a wellbore.

2. The method set forth in claim 1 including the step of:

measuring the pH of said fluid flowing through said sample flow conduit.

3. The method set forth in claim 1 including the step of:

measuring the density of fluid flowing through said sample conduit.

4. The method set forth in claim 1 wherein:

said first manifold includes a first conduit interconnecting said manifold members and a second conduit interconnecting said manifold members and spaced from said first conduit and valve means in said manifold members, respectively, operable to be moved between open and closed positions; and said method includes the step of:

conducting fluid through a selected one of said first and second conduits to maintain a sufficient velocity of fluid flowing through said manifold to minimize the disentrainment of solids in said fluid.

5. The method set forth in claim 1 including the steps of:

providing a second manifold adapted to be interposed between said first manifold and said wellbore, said second manifold including conduit means, flow measuring means interposed in said conduit means for measuring the volumetric flow rate of said fluid, density measuring means interposed in said conduit means for measuring the density of said fluid flowing through said second manifold, and a second sample flow conduit connected to said second manifold and including viscometer means; and determining the viscosity of said fluid after adding a quantity of a solid proppant to said fluid and prior to injection of said fluid into said wellbore.

6. The method set forth in claim 5 wherein:

said system includes a heat exchanger for heating said fluid and viscometer means interposed in a conduit including said heat exchanger and said method includes the step of;

measuring the viscosity of said fluid after a change of temperature is induced in said fluid by said heat exchanger means.

7. The method set forth in claim 5 including the steps of:

measuring the density of fluid flowing through said second manifold; and calculating the shear rate and apparent viscosity of said fluid based on the density of said fluid, the Power Law index and the consistency index.

* * * * *